United States Patent
Tetsuka et al.

(10) Patent No.: US 9,066,773 B2
(45) Date of Patent: Jun. 30, 2015

(54) ROTARY DRIVE CUTTER FOR DENTISTRY

(75) Inventors: Satoshi Tetsuka, Tochigi (JP); Nobuhiro Muraoka, Tochigi (JP); Kazuaki Katoh, Tochigi (JP)

(73) Assignee: MANI, Inc., Utsonomiya-shi, Tochigi (JP)

( * ) Notice: Subject to any disclaimer, the term of this patent is extended or adjusted under 35 U.S.C. 154(b) by 0 days.

(21) Appl. No.: 12/601,222

(22) PCT Filed: May 21, 2008

(86) PCT No.: PCT/JP2008/059318
§ 371 (c)(1),
(2), (4) Date: Nov. 20, 2009

(87) PCT Pub. No.: WO2008/146670
PCT Pub. Date: Dec. 4, 2008

(65) Prior Publication Data
US 2010/0173263 A1 Jul. 8, 2010

(30) Foreign Application Priority Data
May 30, 2007 (JP) ................... 2007-142725

(51) Int. Cl.
*A61C 3/02* (2006.01)
*A61C 5/02* (2006.01)

(52) U.S. Cl.
CPC .. *A61C 3/02* (2013.01); *A61C 5/023* (2013.01)

(58) Field of Classification Search
CPC ......... A61C 3/02; A61C 8/0089; A61C 5/023
USPC .............. 433/165, 102, 81, 224, 166; 606/80, 606/180; 408/199–233
See application file for complete search history.

(56) References Cited

U.S. PATENT DOCUMENTS

| | | | |
|---|---|---|---|
| 2,902,763 A * | 9/1959 | Heppe | 433/165 |
| 4,345,899 A * | 8/1982 | Vlock | 433/165 |
| 5,664,914 A | 9/1997 | Taniguchi | |
| 5,816,807 A | 10/1998 | Matsutani et al. | |

(Continued)

FOREIGN PATENT DOCUMENTS

| | | |
|---|---|---|
| JP | 07299622 A | 11/1995 |
| JP | 11-290344 A | 10/1999 |

(Continued)

OTHER PUBLICATIONS http://en.wikipedia.org/wiki/Parabola retrieved Apr. 12, 2012.*

*Primary Examiner* — Heidi M Eide
(74) *Attorney, Agent, or Firm* — Orion Consulting; Joseph P. Farrar, Esq.

(57) ABSTRACT

A dental rotary drive cutting tool, which can limit breaking location to the shank side, and increase life span until breakage, is provided. A peeso reamer (10) as the dental rotary drive cutting tool according to the present invention includes a cutting portion (11) formed on the tip side, a shank (12) formed in a base, and a neck part (13) formed between the cutting portion (11) and the shank (12), wherein the neck part (13) includes a tapered portion (13*a*), which is wider on the tip side and narrower on the base side, and a straight portion (13*b*), which has a constant thickness with the same diameter as that of the end of the tapered portion on the base side. While it breaks at the narrowest portion of the tapered portion, this portion is a straight portion, and thus increase in life span is possible.

3 Claims, 4 Drawing Sheets

(56) References Cited

U.S. PATENT DOCUMENTS

| | | | |
|---|---|---|---|
| 5,836,764 A * | 11/1998 | Buchanan | 433/102 |
| 2001/0004518 A1 | 6/2001 | Murai et al. | |
| 2002/0119418 A1* | 8/2002 | Matsutani et al. | 433/102 |
| 2003/0159544 A1 | 8/2003 | Moser et al. | |
| 2007/0082318 A1* | 4/2007 | Breguet | 433/102 |

FOREIGN PATENT DOCUMENTS

| | | |
|---|---|---|
| JP | 2001170077 A | 6/2001 |
| JP | 3375771 B | 11/2002 |
| JP | 2003275928 A | 9/2003 |

* cited by examiner

Fig. 4

| | | Peeso reamer | | | Gates drill | | |
|---|---|---|---|---|---|---|---|
| | | Load location: 4.5 mm from the tip for #1, 2, and 3 Pressed amount: 2 mm | | | Load location: 1.5, 1.7 and 1.9mm from tip of #1, #2, and #3, respectively Pressed amount: 2 mm | | |
| | | #1 | #2 | #3 | #1 | #2 | #3 |
| Present invention tool | 1 | 8,639 | 4,256 | 1,968 | 100,000 | 17,266 | 19,297 |
| | 2 | 4,236 | 3,494 | 3,504 | 100,000 | 9,429 | 18,823 |
| | 3 | 9,970 | 4,530 | 3,229 | 100,000 | 16,393 | 7,707 |
| | 4 | 9,315 | 3,242 | 4,082 | 100,000 | 10,835 | 12,253 |
| | 5 | 6,870 | 3,981 | 3,652 | 100,000 | 14,393 | 12,940 |
| | Average | 7,806 | 3,901 | 3,287 | 100,000 | 13,663 | 14,204 |
| | Standard deviation | 2,306 | 531 | 799 | 0 | 3,424 | 4,871 |
| | Maximum | 9,970 | 4,530 | 4,082 | 100,000 | 17,266 | 19,297 |
| | Minimum | 4,236 | 3,242 | 1,968 | 100,000 | 9,429 | 7,707 |
| Conventional tool | 1 | 4,512 | 2,392 | 1,916 | 33,438 | 9,992 | 18,088 |
| | 2 | 5,337 | 4,946 | 2,554 | 20,056 | 13,207 | 8,467 |
| | 3 | 6,471 | 3,262 | 1,988 | 40,002 | 10,215 | 6,980 |
| | 4 | 6,255 | 2,738 | 1,782 | 22,802 | 8,882 | 16,185 |
| | 5 | 3,732 | 3,846 | 1,732 | 33,862 | 17,686 | 5,814 |
| | Average | 5,261 | 3,437 | 1,994 | 30,032 | 11,996 | 11,107 |
| | Standard deviation | 1,157 | 1,007 | 329 | 8,329 | 3,561 | 5,624 |
| | Maximum | 6,471 | 4,946 | 2,554 | 40,002 | 17,686 | 18,088 |
| | Minimum | 3,732 | 2,392 | 1,732 | 20,056 | 8,882 | 5,814 |
| Present invention tool/Conventional tool | | 1.5 | 1.1 | 1.6 | 3.3 | 1.1 | 1.3 |

Rotational frequency: approx. 4,000rpm (4,000 rotations or more)
Note) 100,000 means 100,000 or greater. (Test is halted when exceeding 100,000 rotations)

ROTARY DRIVE CUTTER FOR DENTISTRY

TECHNICAL FIELD

The present invention relates to a dental rotary drive cutting tool such as a peeso reamer or a gates drill.

BACKGROUND ART

In dental care, there are cases of cutting semi-hard layers of dentin or the like formed on a tooth surface and in a root canal where a dental rotary drive cutting tool such as a peeso reamer or a gates drill is used for the purpose of cutting such layer. Here, the peeso reamer and the gates drill only differ in shape of cutting edge formed at the tip, and have the same basic structure and function of cutting tooth dentin.

The tools disclosed in Patent Document 1 (Japanese Patent 3375771) are well known as the peeso reamer or the gates drill. FIG. 5 is a diagram showing the structure of the peeso reamer disclosed in Patent Document 1, and FIG. 6 is an enlarged sectional view cut along a line I-I of FIG. 5. As shown in FIG. 5, a cutting portion 1 is formed along a predetermined length of a peeso reamer A from one end, and a shank 2 having a predetermined length is formed on the other end. A neck part 3 constitutes the part between the cutting portion 1 and the shank 2.

As shown in FIGS. 5 and 6, multiple (3 in the drawings) cutting edges 1a are formed in the cutting portion 1, each of the cutting edges 1a has a preset angle of torsion, and the external shape of the side surface is straight.

The peeso reamer A is rotated and operated by gripping a rotary drive device chuck such as a hand piece or the like, which is omitted from the drawings. For this purpose, the shank 2 has a straight whirl-stop 2a corresponding to the chuck.

The neck part 3 is formed straight having a smaller diameter than outer diameters of the cutting portion 1 and the shank 2, and respective connecting parts on either end with the cutting portion 1 and the shank 2 are formed in an R shape having a predetermined curvature radius.

The aforementioned structure is also for the gates drill. However, in the case of the gates drill, while the corresponding portion to the cutting portion 1 shown in FIG. 5 also has multiple cutting edges with a preset angle of torsion, the angle of torsion (angle between cutting edge and axial center) is large, and the structure in which the external form of the cutting portion formed in a spherical shape differs from that of the peeso reamer.

The peeso reamer A formed as described above is made of austenitic stainless steel. Austenitic stainless steel is excellent in that it does not rust, but it cannot be hardened by quenching. Therefore, in Patent Document 1, austenitic stainless steel wire rod is subjected to a cold wiredrawing process so that the crystal structure is pulled along the line length and made thinner into a fiber structure, work hardened, and then used. Making it into such a fibrous structure allows setting a predetermined hardness of Hv 500 or greater, for example.

Moreover, by axially pulling the composition into fibers through cold wire-drawing, improvement in bending strength and exhibition of uniform strength without any fluctuation across the entire length is possible. The aforementioned wire rod is cut to a length corresponding to the target peeso reamer A, making materials, and the materials are then machined to make the peeso reamer A.

The material obtained by cold wire-drawing austenitic stainless steel has a concentric hardness distribution. In other words, hardness at the surface is highest, and gradually decreases toward the center. Thus, it is hard at the cutting portion 1 and the shank 2 and softer at the neck part 3.

When cutting a root canal with the peeso reamer A structured as described above being attached to a hand piece, since the neck part 3 is narrower and softer than other parts, it bends easily along the root canal curve and rotates in the bent state. The cutting edges 1a cut dentin on the inner wall of the root canal according to this rotation to perform a specific treatment. Since the peeso reamer A rotates in a bent state, a single rotation applies a single-lap bending force on the neck part 3. Through repetitive use, it is bent repeatedly for the number of rotations, and thus the hardness gradually increases and bending fatigue is accumulated. Therefore, the peeso reamer A eventually breaks. However, since the neck part 3 is narrow, the breaking place may be limited to the neck part 3 without breaking at the cutting portion 1 or the shank 2.

When the peeso reamer A breaks at a position near the shank 2 of the neck part 3, the broken end of the neck part 3 protrudes from the root canal. Therefore, the peeso reamer A may be extracted from the root canal by pinching and counter-rotating the protruded portion with pliers or the like. However, if it breaks near the cutting portion 1, the broken portion enters the root canal and cannot be pinched.

As a result, a peeso reamer that has a tapered neck part 5 as shown in FIG. 7 is proposed. This neck part 5 is wider on the cutting portion 1 side and narrower on the shank 2 side. The narrowest portion 5a is near the shank 2. According to this structure, stress when the peeso reamer A is rotated converges at the narrow portion 5a, and when bending fatigue accumulates and it breaks off, the reamer may be easily extracted.
Patent Document 1: Japanese Patent 3375771

DISCLOSURE OF INVENTION

Problems to be Solved by the Invention

However, the conventional technology mentioned above has a problem that it breaks off easier than when the neck part 5 is not tapered.

The present invention is devised through consideration of these problems. An objective thereof is to provide a dental rotary drive cutting tool that can limit breaking locations to the shank side and is difficult to break off.

Means of Solving the Problems

A dental rotary drive cutting tool of the present invention reaching the above-given purpose is characterized in that it includes a cutting portion formed on the tip side, a shank formed in a base, and a neck formed between the cutting portion and the shank. The neck comprises a tapered portion, which is wider on the tip side and narrower on the base side, and a straight portion, which has a constant thickness with the same diameter as that of the end of the tapered portion on the base side.

A connecting part, which gradually becomes thicker towards the shank, may be formed between the straight portion and the shank, or a connecting part, which gradually becomes thicker towards the cutting portion, may be provided between the cutting portion and the tapered portion. Alternatively, the material may have a structure made of austenite stainless steel pulled into fibers.
[Results of Invention]
The dental rotary drive cutting tool according to the present invention is pressed into a curved tooth root canal, rotates in a curved state, and cuts the inner wall of the root canal. Since it rotates in a curved state, the tapered portion is repeatedly bent, and hardness is thus increased, and bending fatigue is accumulated; however, all of this occurs across the entire straight portion. Therefore, beneficial effects such as limiting breaking location to the narrowest tapered portion, and increasing life span until breakage, namely making it difficult to break are achieved.

BRIEF DESCRIPTION OF DRAWINGS

FIG. 4 is a chart giving results of the break test;

DESCRIPTION OF REFERENCE NUMERALS

Figure 1:
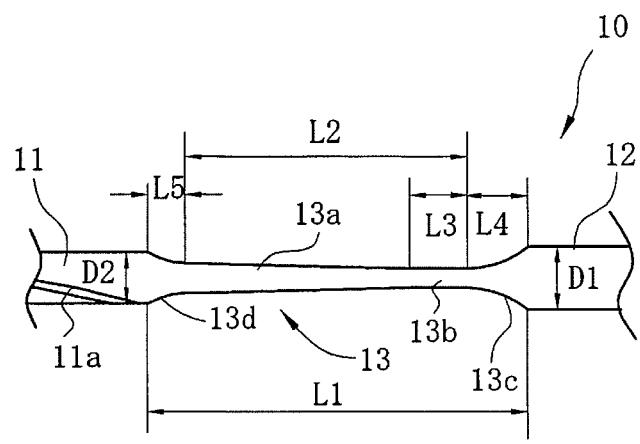
FIG. 1 is a diagram showing principal parts of a peeso reamer of the present invention.

10: Peeso reamer
11: Cutting portion
11a: Cutting edge
12: Shank
13: Neck part
13a: Tapered portion
13b: Straight portion
13c: Connecting part
13d: Connecting part
20: Gates drill
21: Cutting portion
21a: Cutting edge
22: Shank
23: Neck part
23a: Tapered portion
23b: Straight portion
23c: Connecting part

BEST MODE FOR CARRYING OUT THE INVENTION

An embodiment of a dental rotary drive cutting tool according to the present invention is described forthwith with reference to attached drawings.

FIG. 1 is a diagram showing principal parts of a peeso reamer 10 of the present invention. This peeso reamer 10 includes a straight cutting portion 11 at the tip, and a shank 12 at the base. The cutting portion 11 includes multiple cutting edges 11a. Although not shown in the drawings, the shank 12 includes a whirl-stop like the whirl-stop 2a of the conventional example.

While there is a neck part 13 between the cutting portion 11 and the shank 12, this neck part 13 has a tapered portion 13a which is wider on the cutting portion side and is narrower on the shank 12 side. This structure is the same as that in the conventional example described using FIG. 7. The case of the present invention is characteristic in that a straight portion 13b is formed in the narrowest tapered area. A connecting part 13c between the straight portion 13b and the shank 12 is formed in an R shape having a predetermined curvature radius. A similar connecting part 13d is formed between the cutting portion 11 and the tapered portion 13a.

Length of each part will be described. However, dimensions given below are merely examples according to JIS standards and are not limited thereto. In this embodiment, the overall length of the peeso reamer 10 is 32 mm, length of the cutting portion 11 is 8.5 mm, length of the shank 12 is 13 mm, length of the whirl-stop is 2.7 mm, and length L1 of the neck part 13 is 10.5 mm. Diameter D1 of the shank 12 is 2.35 mm, and there are six kinds of diameters D2 of the cutting portion 11 ranging from 0.85 mm to 1.85 mm. With the dimensions of each part given above, length L2 of the tapered portion 13a is 6.45 to 7.2 mm, where there are six kinds of diameters ranging in width from 0.55 to 1.05 mm in accordance with the diameter of the cutting portion 11, difference between the long diameter and short diameter is 0.04 mm, and length L3 of the straight portion 13b is 1.0 mm. Moreover, length L4 of the connecting part 13c is 2.8 mm and length L5 of the connecting part 13d is from 0.5 to 1.25 mm.

Figure 7:
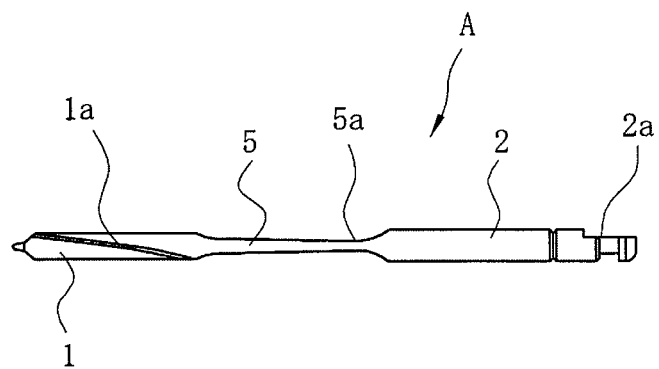
FIG. 7 is a diagram of a conventional peeso reamer having a tapered neck part.

Since the conventional tapered neck part 5 shown in FIG. 7 has an R-shaped connecting part from the narrowest portion 5a, the narrowest portion 5a is limited to one axial point. In the case of cutting a root canal, the neck part 5 rotates in a curved state, and increase in hardness and accumulation of bending fatigue at this time concentrates at this narrowest point. Thus, it is easily broken at an early stage.

Meanwhile, according to the present invention, the length of the straight portion 13b or the narrowest portion is 1.0 mm. As a result, increase in hardness and accumulation of bending fatigue occurs across the entire straight portion 13b, taking a long time until breakage.

Figure 2:
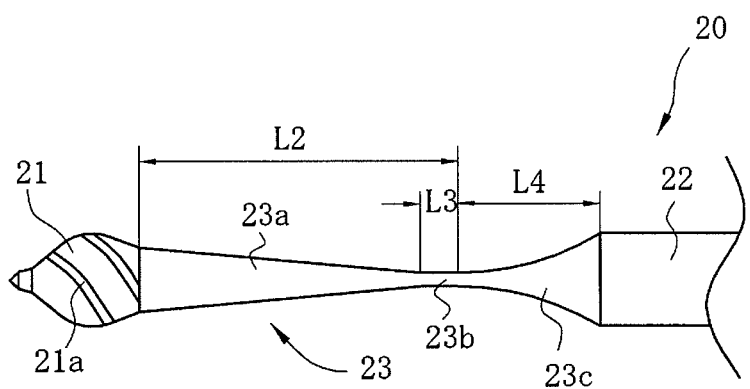
FIG. 2 is a diagram showing principal parts of a gates drill of the present invention.

FIG. 2 is a diagram showing principal parts of a gates drill 20 according to the present invention. This gates drill 20 includes a bulb-shaped cutting portion 21 at the tip, and a shank 22 at the base. The cutting portion includes multiple cutting edges 21a. The angle of torsion of the cutting edges 21a (angle between cutting edge and axial center) is larger than that of the cutting edges 11a of the peeso reamer 10. Although not shown in the drawings, the shank 22 includes a whirl-stop like the whirl-stop 2a of the conventional example. In the embodiment shown in the drawing, there is no R-shaped connecting part having a predetermined curvature radius between the cutting portion 21 and a neck part 23.

While the neck part 23 is between the cutting portion 21 and the shank 22, this neck part 23 having a tapered portion 23a which is wider on the cutting portion 21 side and is narrower on the shank 22 side is the same as in the conventional example described using FIG. 7. With the present invention, a straight portion 23b is formed in the narrowest tapered area. A connecting part 23c between the straight portion 23b and the shank 22 is formed in an R shape having a predetermined curvature radius. However, in the embodiment shown in the drawing, there is no R-shaped connecting part having a predetermined curvature radius between the cutting portion 21 and the neck part 23. Length L3 of the straight portion 23b is 1 mm, which is the same as in the case of the peeso reamer 10 of FIG. 1.

Note that since breakage easily occurs due to too short a length of L3, which suppresses superiority, and tilt of the tapered portions 13a and 23a increases when it is too long, stress concentrates at the boundaries between the tapered portion 13a and the straight portion 13b and the tapered portion 23a and the straight portion 23b, respectively, making it easier to break. The length of L3 should be selected appropriately according to instrument to be used or usage thereof. According to the experiment by the inventor(s), if L3 exceeds 0.5 mm, better advantages may be acquired than with the conventional tool, and if it is less than 2 mm, tilt of the tapered portions 13a and 23a may be made not so large, making it difficult to break.

Next, how to conduct a fatigue break test will be described.

If a dental rotary drive cutting tool is rotated in a curved state and rotations per minute is increased, it will break over time. It is known that there is correlation between rotations per minute at the time of this breakage and life span. In other words, when breaking rotational frequency is small, the life span is short, and when breaking rotational frequency is large, life span is long. Therefore, a break test as given below was conducted.

Figure 3:
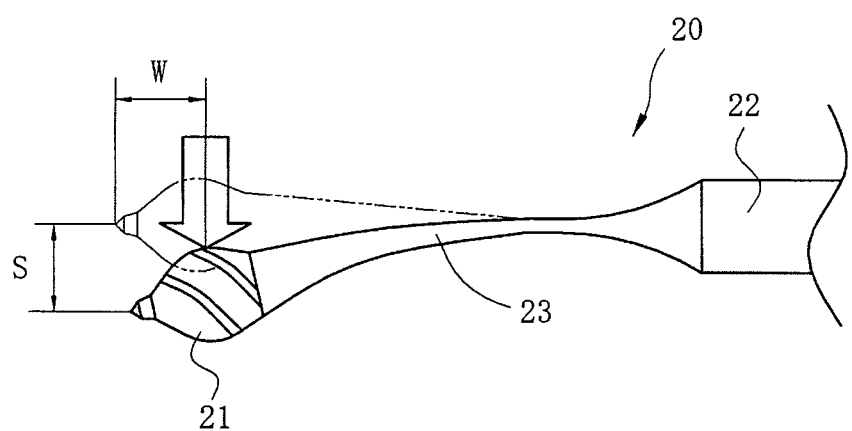
FIG. 3 is a diagram describing conditions for a break test.
Figure 5:
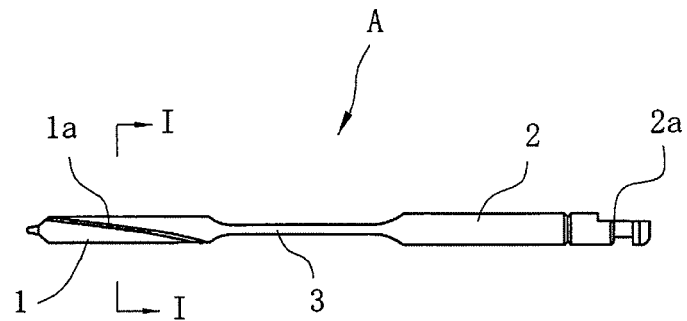
FIG. 5 is a diagram showing the structure of the peeso reamer disclosed in Patent Document 1.
Figure 6:
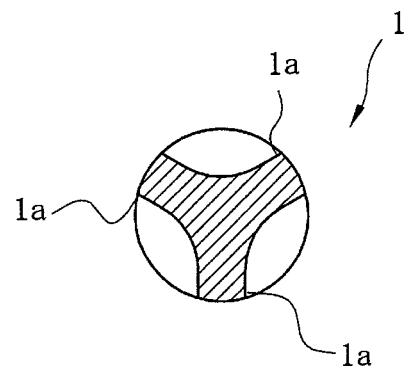
FIG. 6 is an enlarged sectional view cut along a line I-I of FIG. 5.

FIG. 3 is a diagram describing conditions for the break test. As illustrated with the gates drill 20, the shank 22 of the gates drill 20 is grasped and kept level, a load is applied to a predetermined location from the tip, and is rotated in a state vertically lowered to only a predetermined distance. The length of the peeso reamer and the gates drill is 32 mm, and diameters indicate those of the cutting portion 21, which are: #1 is φ0.5 mm, #2 is φ90.7 mm, and #3 is φ0.9 mm.

Distance W from the tip to the location in which a load is applied is 4.5 mm for all types of the peeso reamer. In the case of the gates drill, distances W are: #1 is 1.5 mm, #2 is 1.7 mm, and #3 is 1.9 mm. Distance (pressed amount) S that it is lowered vertically is 2 mm for all.

When diameters #1, #2, and #3 of five of each of the conventional tool, which does not include the straight portions 13b and 23b, and the present invention formed with the straight portions 13b and 23b are tested under the above-given conditions, broken locations are all either at the straight portions or the narrowest tapered locations. Rotational frequencies at the time of breakage are given in a chart.

FIG. 4 is the chart giving results of the break test. Numbers written in each column are rotations per minute at the time of breakage. Those on the upper side are for the present invention, and those on the lower side are for the conventional tool. The narrowest edge #1 of the gates drill of the present invention did not break even when the rotations per minute reached one hundred thousand times. Moreover, for #1, #2 and #3, the life span of the structure according to the present invention including the straight portions is increased. Particularly, the narrowest #1 had a remarkable tendency for a longer life span.

Next, torsional torque will be described.

In general, since rigidity is weak if it is a material with good fatigue breaking characteristics (which means it has a long life span), maximum torsional torque tends to be small. However, this time, when a fatigue breaking test and a torsional torque test are conducted, almost the same results as for the conventional tool are attained even in the torsional torque test. Reasons considered are that the material is a fibrous composition made of austenitic stainless steel, and stress is dispersed across the whole straight portion.

First, attach an end of the tool to a steel chuck and tighten it. Next, hold the other end with a brass chuck, confirm that the centers of both chucks are on the same axis and tighten them, hold the steel chuck and set so as for a reversible gear motor to rotate at two rotations per minute, and check the maximum torsional torque until breakage using a torsional resistance gauge provided on the brass chuck side.

Diameters #1, #2, and #3 of five of each of the conventional tool, which does not include the straight portions 13b and 23b, and the present invention formed with the straight portions 13b and 23b are tested under the above-given conditions. With both the peeso reamer and the gates drill, #1, #2, and #3 all give the same or slightly higher results than the conventional tool. Torque for #1 of the peeso reamer is 476 gcm for the conventional tool and 493 gcm for the present invention, and torque for #1 of the gates drill is 244 gcm for the conventional tool and 250 gcm for the present invention, where the torque for the present invention is 1.03 times greater than that of the conventional tool.

The invention claimed is:

1. A dental rotary drive cutting tool, comprising:
a cutting portion formed on a tip side,
a shank formed in a base, and
a neck part formed between the cutting portion and the shank;
wherein the neck part comprises a tapered portion, which is wider on the tip side and narrower on a side closer to the base, and the neck part includes a straight portion, which has a constant thickness along the length of the straight portion and a smooth surface; wherein the straight portion has a diameter equal to a diameter of an end of the tapered portion on the side closer to the base, and the neck part includes a connecting part between the straight portion and the shank, which gradually becomes thicker towards the shank,
wherein a length of the straight portion is 0.5 to 2.0 mm.

2. A reamer, comprising:
a peeso reamer comprising a cutting portion formed on a tip side,
a shank formed in a base, and
a neck part formed between the cutting portion and the shank;
wherein the neck part comprises a tapered portion, which is wider on the tip side and narrower on a side closer to the base, and the neck part includes a straight portion, which has a constant thickness along the length of the straight portion and a smooth surface; wherein the straight portion has a diameter equal to a diameter of an end of the tapered portion on the side closer to the base, and the neck part includes a connecting part between the straight portion and the shank, which gradually becomes thicker towards the shank,
wherein a length of the straight portion is at least 0.5 mm and at most 2.0 mm.

3. A drill, comprising:
a gates drill comprising a cutting portion formed on a tip side,
a shank formed in a base and having a whirl-stop formed therein, and
a neck part formed between the cutting portion and the shank;
wherein the neck part comprises a tapered portion, which is wider on the tip side and narrower on a side closer to the base, and the neck part includes a straight portion, which has a constant thickness along the length of the straight portion and a smooth surface; wherein the straight portion has a diameter equal to a diameter of an end of the tapered portion on the side closer to the base, and the neck part includes a connecting part between the straight portion and the shank, which gradually becomes thicker towards the shank,
wherein a length of the straight portion is at least 0.5 mm and at most 2.0 mm.

* * * * *